United States Patent
Narayan

(10) Patent No.: US 11,746,016 B2
(45) Date of Patent: Sep. 5, 2023

(54) DIRECT CONVERSION OF TEFLON TAPE INTO DIAMOND, Q-CARBON, AND GRAPHENE FILMS

(71) Applicant: North Carolina State University, Raleigh, NC (US)

(72) Inventor: Jagdish Narayan, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 268 days.

(21) Appl. No.: 17/335,164

(22) Filed: Jun. 1, 2021

(65) Prior Publication Data

US 2021/0380412 A1  Dec. 9, 2021

Related U.S. Application Data

(60) Provisional application No. 63/036,635, filed on Jun. 9, 2020.

(51) Int. Cl.
  *C01B 32/05* (2017.01)
  *C01B 32/184* (2017.01)
  (Continued)

(52) U.S. Cl.
  CPC ............ *C01B 32/05* (2017.08); *A61F 2/3094* (2013.01); *B29C 64/188* (2017.08); *B29C 71/02* (2013.01);
  (Continued)

(58) Field of Classification Search
  CPC ....... C01B 32/05; C01B 32/184; C01B 32/26; A61F 2/3094; A61F 2002/3097;
  (Continued)

(56) References Cited

U.S. PATENT DOCUMENTS

| 10,566,193 B2 | 2/2020 | Narayan | |
| 2013/0243965 A1* | 9/2013 | Choi | C01B 32/184 |
| | | | 427/504 |

(Continued)

FOREIGN PATENT DOCUMENTS

JP  2004123420 A  *  4/2004  .........  C03B 19/1453

OTHER PUBLICATIONS

Laser-Induced Conversion of Teflon into Fluorinated Nanodiamonds or Fluorinated Graphene Ruquan Ye, Xiao Han, Dmitry V. Kosynkin, Yilun Li, Chenhao Zhang, Bo Jiang, Angel A. Martí, and James M. Tour ACS Nano 2018 12 (2), 1083-1088 DOI: 10.1021/acsnano. 7b05877 (Year: 2018).*

(Continued)

*Primary Examiner* — Leith S Shafi
*Assistant Examiner* — Inja Song
(74) *Attorney, Agent, or Firm* — Clements Bernard Walker; Jennifer R. Knight

(57) ABSTRACT

In various exemplary embodiments, the present disclosure provides a process for the conversion of certain polymers into diamond and diamond-like materials using laser pulse annealing. The process includes transforming the polymer to carbon, melting the carbon and quenching the carbon melt into to form Q-carbon, diamond, and/or graphene. The process can be applied to a polymer film such as a polytetrafluoroethylene (PTFE) tape. An object can be coated with the polymer film which can then be converted to Q-carbon, diamond, and/or graphene using laser pulse annealing. A process is also provided for making a three-dimensional object using a combination of, for example, 3D printing the polymer and converting each layer of polymer into Q-carbon, diamond and/or graphene.

20 Claims, 10 Drawing Sheets

(51) Int. Cl.
  *A61F 2/30* (2006.01)
  *B33Y 10/00* (2015.01)
  *B33Y 40/20* (2020.01)
  *B29C 71/04* (2006.01)
  *B29C 71/02* (2006.01)
  *B29C 64/188* (2017.01)
  *C01B 32/26* (2017.01)
  *B29K 27/18* (2006.01)

(52) U.S. Cl.
  CPC .............. *B29C 71/04* (2013.01); *B33Y 10/00* (2014.12); *B33Y 40/20* (2020.01); *C01B 32/184* (2017.08); *C01B 32/26* (2017.08); *A61F 2002/3097* (2013.01); *A61F 2002/30971* (2013.01); *A61F 2002/30985* (2013.01); *A61F 2310/0058* (2013.01); *A61F 2310/00586* (2013.01); *B29C 2071/025* (2013.01); *B29K 2027/18* (2013.01)

(58) Field of Classification Search
  CPC .. A61F 2002/30971; A61F 2002/30985; A61F 2310/0058; A61F 2310/00586; B29C 64/188; B29C 71/02; B29C 71/04; B29C 2071/025; B33Y 10/00; B33Y 40/20; B29K 2027/18
  See application file for complete search history.

(56) References Cited

U.S. PATENT DOCUMENTS

2017/0037530 A1\* 2/2017 Narayan .................. C01B 32/26
2019/0330064 A1\* 10/2019 Tour ...................... B01D 71/021

OTHER PUBLICATIONS

English translation of JP-2004123420-A (OA Appendix). (Year: 2004).\*

\* cited by examiner

DIRECT CONVERSION OF TEFLON TAPE INTO DIAMOND, Q-CARBON, AND GRAPHENE FILMS

CROSS-REFERENCE

This application claims priority to U.S. Provisional Application Ser. No. 63/036,635 filed on Jun. 9, 2020, which is incorporated herein by reference in its entirety.

This invention was made with government support under grant number DMR1735695 awarded by the National Science Foundation. The government has certain rights in the invention.

FIELD

The invention relates generally to synthesis and processing of materials and nanostructures, and more particularly to synthesis and processing of thin films of polymers directly into Q-carbon, diamond and/or graphene films. The invention also relates to the 3D printing of polymer films and the conversion of each layer of polymer film into Q-carbon, diamond and/or graphene to produce an extremely hard and resistant object from a polymer.

BACKGROUND

Diamond is an extraordinary material because of its exceptional mechanical, optical, and electronic properties. It exhibits record thermal conductivity (220 W/cm K) with a wide-band gap of 5.47 eV. Single-crystalline diamond is an ultimate semiconductor, considering its record Johnson (8200) and Keyes (32) figures of merit relevant for high-power and microelectronic devices, respectively, compared to 1 for Si. Particularly of interest are the NV and SiV nanodiamonds, which provide an ideal platform for quantum computing and nanosensing. The biocompatibility and scope of functionalization in nanodiamonds makes them an attractive option for usage in drug delivery and nanomechanical devices. However, diamond is metastable at ambient conditions presenting formidable processing challenges in the fabrication of high-quality thin films. The idea of surface modification of these materials in ambient conditions and the consequent amorphous to crystalline transformation has driven decades of research. The direct conversion of graphite into diamond via equilibrium route requires very high temperature and pressure (HPHT) conditions: 5000 K and 12 GPa, respectively. These HPHT values can be lowered somewhat by using catalysts.

Nonequilibrium processing based shockwave-assisted processing, detonation with explosive, and selective etching of SiC approaches have resulted in limited diamond yield with increased defect inclusions, impurity contamination, and poor control on microstructure. The formation of diamond thin films and related structures for solid-state devices relies on chemical vapor deposition (CVD) processing, where diamond thin films are often contaminated with $sp^2$ bonded carbon.

U.S. Pat. No. 10,566,193 discloses, among other things, the phase transformation of an amorphous carbon film into diamond, Q-carbon, and/or graphene in ambient conditions utilizing liquid-phase regrowth of the super undercooled molten carbon at a temperature less than 4000K. The film can be deposited on a substrate by pulsed laser deposition. The melting can include melting at least a portion of the material using a nanosecond laser pulse. The melting and/or quenching can be performed in an environment at ambient temperature and pressure. U.S. Pat. No. 10,566,193 is incorporated herein by reference in its entirety.

There is a need to produce diamond and diamond-like films in an environment of ambient temperature and pressure that eliminates the expensive step of using pulsed laser deposition to make the initial film. There is a need for a process to readily coat an object and convert the coating to a diamond or diamond-like coating. There is also the need to be able to readily build specialized diamond and diamond-like tools and objects.

SUMMARY OF THE INVENTION

According to an exemplary embodiment of the invention, a process is provided. The process includes the steps of a) increasing the absorbance of an unconverted section of a thin polymer film by at least one conditioning laser pulse to produce a lasered section; b) melting the lasered section at a temperature of about 4000K by a conversion laser pulse; and c) quenching the melted lasered section to form a quenched section comprising Q-carbon, diamond, and/or graphene. Steps a) through c) occur in an environment at ambient temperature and pressure. The polymer film comprises a polymer selected from the group consisting of polyethylene (PE), polyvinyl chloride (PVC), polytetrafluoroethylene (PTFE), polystyrene (PS), and/or polypropylene (PP).

According to another exemplary embodiment of the invention, a process is provided for coating an object. The process includes the steps of a) applying a thin polymer film to at least a portion of an object; b) increasing the absorbance of an unconverted section of the thin polymer film by at least one conditioning laser pulse to produce a lasered section; c) melting the lasered section at a temperature of about 4000K by a conversion laser pulse; d) quenching the melted lasered section to form an initial quenched section comprising Q-carbon, diamond, and/or graphene; e) adjusting the object with the applied thin polymer film and at least one quenched section and/or the laser positioning mechanism such that the conditioning laser pulse strikes a subsequent unconverted section of the thin polymer film; f) increasing the absorbance of the subsequent unconverted section of the thin polymer film by the at least one conditioning laser pulse to produce a subsequent lasered section; g) melting the subsequent lasered section at a temperature of about 4000K by the conversion laser pulse; h) quenching the melted subsequent lasered section to create a subsequent quenched section comprising Q-carbon, diamond, and/or graphene; and repeating steps e) through h) until a final desired portion of the thin polymer film is converted to the finished quenched section. The finished quenched section comprises the initial quenched section and each of the subsequent quenched sections. Steps b) through d) and steps f) through h) occur in an environment at ambient temperature and pressure. The thin polymer film comprises a polymer selected from the group consisting of polyethylene (PE), polyvinyl chloride (PVC), polytetrafluoroethylene (PTFE), polystyrene (PS), and/or polypropylene (PP).

According to another exemplary embodiment of the invention, a process is provided for making a three-dimensional object. The process includes the steps of a) applying a first layer of a thin polymer film on a substrate; b) increasing the absorbance of an unconverted section of the thin polymer film by at least one conditioning laser pulse to produce a lasered section; c) melting the lasered section at a temperature of about 4000K by a conversion laser pulse; quenching the melted lasered section to form a first quenched section comprising Q-carbon, diamond, and/or graphene; e) adjusting the thin polymer film and at least one quenched section and/or the laser positioning mechanism such that the conditioning laser pulse strikes a subsequent unconverted section of the thin polymer film; f) increasing the absorbance of the subsequent unconverted section of the thin polymer film by the at least one conditioning laser pulse to produce a subsequent lasered section; g) melting the subsequent lasered section at a temperature of about 4000K by the at least one conversion laser pulse; h) quenching the melted subsequent lasered section to form a subsequent quenched section comprising Q-carbon, diamond, and/or graphene; i) repeating steps e) through h) until a final desired portion of the thin polymer film is converted to the finished quenched section, wherein the finished quenched section comprises the initial quenched section and each of the subsequent quenched sections; j) applying a subsequent layer of the thin polymer film in a predetermined pattern to form the three-dimensional object and repeating steps b) through i); and k) repeating step j) until the three-dimensional object is completed. Steps b) through d) and steps f) through h) occur in an environment at ambient temperature and pressure. The polymer film comprises a polymer selected from the group consisting of polyethylene (PE), polyvinyl chloride (PVC), polytetrafluoroethylene (PTFE), polystyrene (PS), and/or polypropylene (PP).

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION

Figure 1:
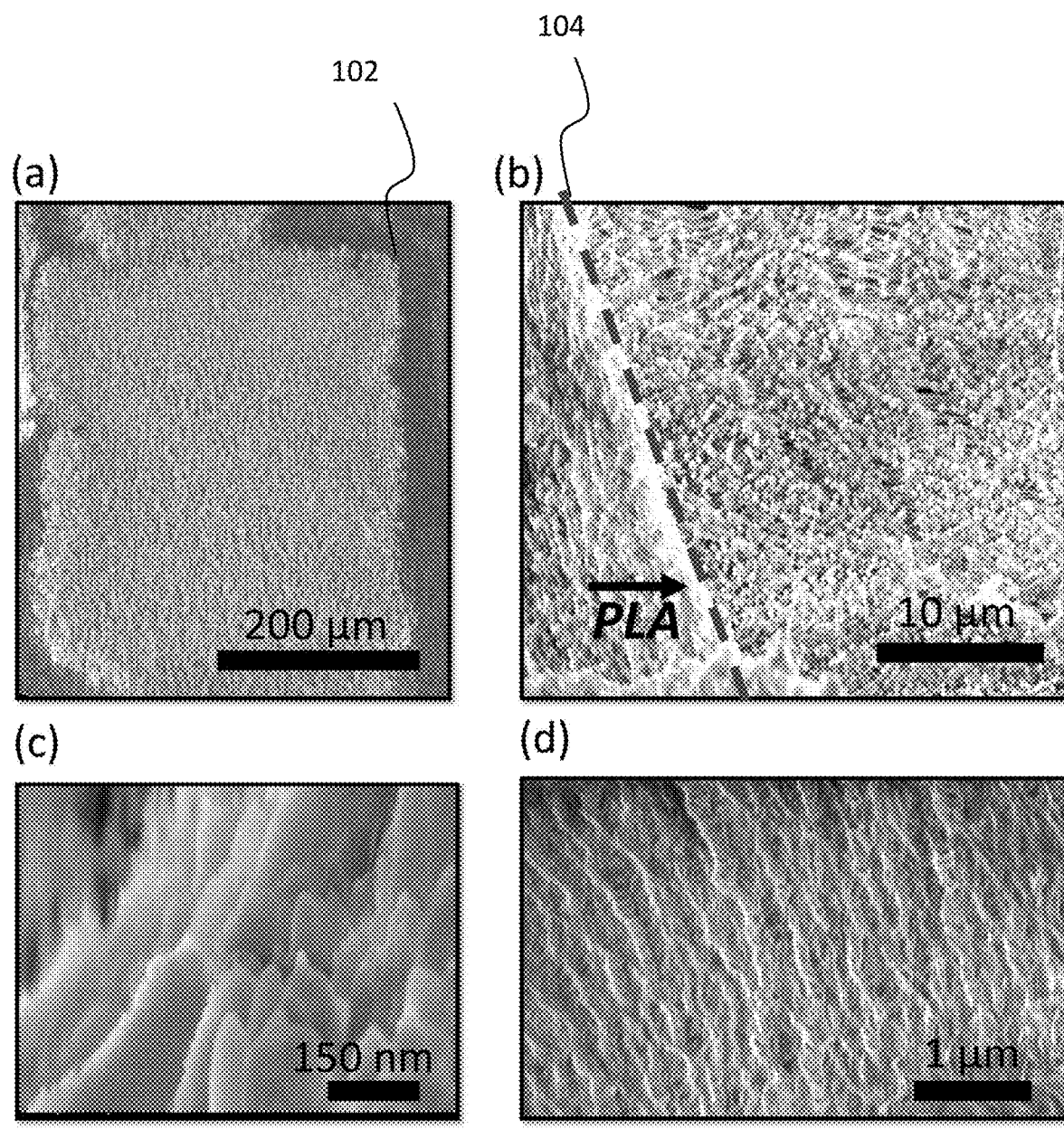
FIG. 1. Is a top view of a scanning electron microscope ("SEM") micrographs (a) revealing the laser patterned boundary on pulsed laser annealing (PLA) processed Teflon film on (0001) $Al_2O_3$, made by performing shadow masking, (b) revealing the 50° tilt-corrected FESEM secondary electron imaging of the irradiated nanodiamond region/PTFE boundary, (c) revealing the high-resolution imaging of the nanodiamonds formed on PLA processing, and (d) revealing the as-acquired PTFE tape with no presence of diamonds before laser annealing.

The present invention provides in an exemplary embodiment a process including the steps of a) increasing the absorbance of an unconverted section of a thin polymer film by at least one conditioning laser pulse to produce a lasered section; b) melting the lasered section at a temperature of about 4000K by a conversion laser pulse; and c) quenching the melted lasered section to create a Q-carbon, diamond, and/or graphene quenched section. Steps a) through c) occur in an environment at ambient temperature and pressure. The polymer film comprises a polymer selected from the group consisting of polyethylene (PE), polyvinyl chloride (PVC), polytetrafluoroethylene (PTFE), polystyrene (PS), and/or polypropylene (PP).

It is to be understood that the mention of one or more method steps does not preclude the presence of additional method steps before or after the combined recited steps or intervening method steps between those steps expressly identified. Moreover, the lettering of method steps or ingredients is a conventional means for identifying discrete activities or ingredients and the recited lettering can be arranged in any sequence, unless otherwise indicated.

As used herein, the term "and/or", when used in a list of two or more items, means that any one of the listed items can be employed by itself, or any combination or two or more of the listed items can be employed. For example, if a composition is described as containing compounds A, B, "and/or" C, the composition may contain A alone; B alone; C alone; A and B in combination; A and C in combination; B and C in combination; or A, B, and C in combination.

As used herein, the term, "conditioning laser pulse", refers to the one or more laser pulses that strike the thin polymer film and increase the absorbance of the film without melting. The term, "conversion laser pulse", as used herein, refers to the laser pulse that melts the carbon of the film.

As used herein, the term, "Q-carbon", refers to a phase of solid carbon with a density of ~5.0 g/cc, and a mixture of randomized fourfold (75%-85%) $sp^3$ bonded carbon and remaining $sp^2$ bonded carbon.

As used herein, the term "unconverted section" refers to any part of the thin polymer film that has not previously been struck by at least one laser pulse.

The present embodiment comprises a) increasing the absorbance of an unconverted section of a thin polymer film by at least one conditioning laser pulse to produce a lasered section. The polymer film comprises a polymer. The polymer can be polyethylene $(C_2H_4)_n$, polyvinyl chloride $(C_2H_3Cl)_n$, polytetrafluoroethylene $(C_2F_4)_n$, polystyrene $(C_8H_8)_n$, and/or polypropylene $(C_3H_6)_n$. In some aspects, the polymer is selected from a group consisting of polyethylene (PE), polyvinyl chloride (PVC), polytetrafluoroethylene (PTFE), polystyrene (PS), and/or polypropylene (PP). In some aspects, the polymer consists of polytetrafluoroethylene. In some aspects, the polymer comprises polytetrafluoroethylene. In some aspects, the polymer film is part of a polytetrafluoroethylene tape. In some aspects, the polytetrafluoroethylene is doped with elements. Non-limiting example of elements includes nickel. The degree of polymerization of the polymer (i.e., the number of repeating units) is not particularly limiting as long as the polymer can be formed into a thin film. In some aspects, the thin polymer film thickness ranges from 5 nm to 500 nm.

The absorbance of the polymer is lower than the absorbance of carbon. The polymer first unzips into monomers and dimers with the at least one conditioning laser pulse. The absorbance increases with each subsequent conditioning laser pulse.

In some aspects, the conditioning laser pulse can have a wavelength ranging from 193 nm to 308 nm. In some aspects, the conditioning laser pulse can have a duration ranging from 20 ns to 60 ns. The at least one conditioning laser pulse strikes the unconverted section of the thin polymer film for the duration to increase the absorbance.

The present embodiment comprises b) melting the lasered section at a temperature of about 4000K by a conversion laser pulse. In some aspects, the conversion laser pulse can have a wavelength ranging from 193 nm to 308 nm. In some aspects, the conversion laser pulse can have a duration ranging from 20 ns to 60 ns.

The wavelength of the at least one conditioning laser pulse and the wavelength of the conversion laser pulse can be same or different. The duration of the at least one conditioning laser pulse and the duration of the conversion layer pulse can be same or different. In some aspects, the wavelength and/or duration of the condition laser pulse and the wavelength and/or duration of the conversion laser pulse are the same.

The present embodiment comprises c) quenching the melted lasered section to form a quenched section comprising Q-carbon, diamond, and/or graphene. When the laser pulses cease, the small area of melted lasered section rapidly cools, or quenches. The quenching is influenced by material characteristics and process parameters. Non-limiting examples of factors impacting quenching include the temperature of the melted laser section, the energy density and duration of the conversion laser pulse, the thickness of the melted laser section, and the thermal conductivity of any substrate. In some aspects, the quenched section comprises diamond. In some aspects, the quenched section comprises graphene. In some aspects, the quenched section comprises Q-carbon. In some aspects, the quenched section comprises a composite of C-carbon and diamond. In some aspects, quenching the melted lasered section from a temperature of around 4000K creates a quenched section comprising Q-carbon, diamond, and/or Q-carbon/diamond composite. In some aspects, melting of the lasered section occurs at a temperature slightly above 4000K and quenching the melted lasered section results in a quenched section comprising diamond. In some aspects, melting of the lasered section occurs at a temperature slightly below 4000K and quenching the melted lasered section results in a quenched section comprising Q-carbon.

The heat flow of the at least one conditioning laser pulse and the conversion laser pulse is spatially and temporally confined. As such, the lasered section can be melted at a temperature of about 4000K in an environment of ambient conditions. In some aspects, steps a) through c) occur in an environment at ambient temperature and pressure. In some aspects, ambient temperature ranges from 10° C. to 100° C. In some aspects, ambient pressure ranges from 0.5 bar to 2 bar. In some aspects, ambient temperature is room temperature and ambient pressure is atmospheric. Steps a)-c) can be referred to as pulsed laser annealing (PLA).

In some aspects, the thin polymer film is proximate to a substrate. The substrate is not particularly limiting. In some aspects, the substrate is selected from the group consisting of metals, semiconductors, ceramics, and glass. In some aspects the substrate is selected from the group consisting of copper, nickel, titanium, titanium cobalt, stainless steel, cobalt-chromium alloys, titanium carbide, tungsten carbide, and titanium/cobalt mixed metal. In some aspects, the substrate is selected from the group consisting of silicon, germanium, gallium arsenide, zinc oxide, gallium nitride and gallium oxide. In some aspects, the substrate is selected from the group consisting of aluminum oxide and magnesium oxide. In some aspects, the substrate is glass. In some aspects, the polymer film and the substrate are in the form of a tape.

In some aspects, the substrate is an object, and the thin polymer film is a coating encompassing the object. Non-limiting examples of the object of some aspects include tools such as blades and drill bits and artificial joint replacements such as hip, knee, ankle, wrist, shoulder, and elbow. In some aspects the object is selected from the group consisting of sapphire windows and mobile device screens (such as cell phone screens).

In some aspects, the process further comprises steps d) through h). In some aspects, the process further comprises d) adjusting the thin polymer film and the at least one quenched section and/or the laser positioning mechanism such that the conditioning laser pulse strikes a subsequent unconverted section of the thin polymer film. In some aspects, the thin polymer film and the at least one quenched section are physically moved such that the conditioning laser beam strikes an unconverted section of the thin polymer film. In some aspects, the conditioning laser beam starting point is physically adjusted such that the laser beam strikes an unconverted section of the thin polymer film. In some aspects, the laser beam path is adjusted (e.g., with mirrors) such that the laser beam strikes an unconverted section of the thin polymer film.

In some aspects, the process further comprises e) increasing the absorbance of the subsequent unconverted section of the thin polymer film by the at least one conditioning laser pulse to produce a subsequent lasered section; f) melting the subsequent lasered section at a temperature of about 4000K by the conversion laser pulse; and g) quenching the melted subsequent lasered section to form a subsequent quenched section comprising Q-carbon, diamond, and/or graphene.

In some aspects, the process further comprises h) repeating steps d) through g) until a final desired portion of the thin polymer film is converted to the finished quenched section comprising Q-carbon, diamond, and/or graphene. The finished quenched sections comprise the initial quenched section and each of the subsequent quenched sections. In some aspects, the finished quenched section comprises diamond. In some aspects, the finished quenched section comprises graphene. In some aspects, the finished quenched section comprises Q-carbon. In some aspects, the finished quenched section comprises a composite of Q-carbon and diamond.

In some aspects, quenching the melted lasered section from a temperature of around 4000K creates a quenched section comprising Q-carbon, diamond, and/or Q-carbon/diamond composite. In some aspects, melting of the laser section occurs at a temperature slightly above 4000K and quenching the melted lasered section results in a quenched section comprising diamond. In some aspects, melting of the laser section occurs at a temperature slightly below 4000K and quenching the melted lasered section results in a quenched section comprising Q-carbon.

In some aspects, the finished quenched section is contiguous. In some aspects, the finished quenched section comprises diamond in the form of at least one nanodiamond, microdiamond, nanoneedle, microneedle, or large area single crystal film. In some aspects, the diamond can comprise at least one nanodiamond ((e.g., a diamond that has a size range of less than 100 nanometers (nm)). In some aspects, the diamond can comprise at least one microdiamond (e.g., a diamond that has a size range of greater than 100 nm to about 1000 nm). In some aspects diamond is in the form of a nanoneedle or microneedle. In some aspects, a diamond microneedle can have a length of up to 2000 nm. In some aspects, a diamond microneedle or diamond nanoneedle may be a diamond with a diameter between 80 nm to 500 nm and a length between 2000 nm to 3000 nm. In some aspects, the nanodiamonds formed can be used for nanosensing, quantum communication, and quantum computing.

In some aspects, steps e) through g) occur in an environment at ambient temperature and pressure. In some aspects, ambient temperature ranges from 10° C. to 100° C. In some aspects, ambient pressure ranges from 0.5 bar to 2 bar. In some aspects ambient temperature is room temperature and ambient pressure is atmospheric.

As much of the thin polymer film as desired can be processed into quenched sections comprising Q-carbon, diamond, and/or graphene. In some aspects 10% to 100% of the thin polymer film is converted to the quenched sections based upon the surface area of the thin polymer film. Other, non-limiting examples of the amount of the thin polymer film converted to quenched sections comprising Q-carbon, diamond, and/or graphene include 25% to 100%, 50% to 100%, 75% to 100%, 10% to 99%, 50% to 99%, and 75% to 99%.

In another embodiment of the invention a process for coating an object comprises steps a) through i). The process comprises a) applying a thin polymer film to at least a portion of an object; b) increasing the absorbance of an unconverted section of the thin polymer film by at least one conditioning laser pulse to produce a lasered section; c) melting the lasered section at a temperature of about 4000K by a conversion laser pulse; d) quenching the melted lasered section to form an initial quenched section comprising Q-carbon, diamond, and/or graphene; e) adjusting the object with the applied thin polymer film and at least one quenched section and/or the laser positioning mechanism such that the conditioning laser pulse strikes a subsequent unconverted section of the thin polymer film; f) increasing the absorbance of the subsequent unconverted section of the thin polymer film by the at least one conditioning laser pulse to produce a subsequent lasered section; g) melting the subsequent lasered section at a temperature of about 4000K by the conversion laser pulse; h) quenching the melted subsequent lasered section to create a subsequent quenched section comprising Q-carbon, diamond, and/or graphene; and i) repeating steps e) through h) until a final desired portion of the thin polymer film is converted to the finished quenched section. The finished quenched section comprises the initial quenched section and each of the subsequent quenched sections. Steps b) through d) and steps f) through h) occur in an environment at ambient temperature and pressure. The thin polymer film comprises a polymer selected from the group consisting of polyethylene (PE), polyvinyl chloride (PVC), polytetrafluoroethylene (PTFE), polystyrene (PS), and/or polypropylene (PP).

It is to be understood that the various aspects of the thin polymer film; the increasing of the absorbance by at least one conditioning laser pulse; the melting of the lasered section by a conversion laser pulse; the quenching of the melted laser section to form a quenched section comprising Q-carbon, diamond, and/or graphene; the forms of diamonds; the characteristics of the conditioning laser pulse and the conversion laser pulse; the environment at ambient temperature and pressure; and the final desired portion of the polymer film converted, described herein above, apply to the present embodiment as well.

In some aspects, a) applying a thin polymer film to at least a portion of the object includes 3D printing the thin polymer film on the object. In some aspects, the object is encompassed by the thin polymer film. In some aspects, the thin polymer film comprises polytetrafluoroethylene (PTFE) which is 3D printed on the object.

In some aspects, step a), the application of the thin polymer film, is performed separately from, and completed prior to, the Pulsed Laser Annealing (PLA) of steps b)-i). In some aspects, steps a) and steps b) through i) are performed in tandem. For example, a thin polymer film can be continuously 3D printed onto an object and PLA steps b) through i) can be performed on the recently-printed section of the thin polymer film. In some aspects, the thin polymer film forms a coating encompassing the object. In some aspects, the finished quenched section comprising Q-carbon, diamond, and/or graphene is contiguous.

The object to be coated with the thin polymer film is not particularly limiting. In some aspects, that object can be made of a single material or composite throughout. In some aspects, the object can have an outer surface that is made of a different material than the rest of the object. For the PLA, steps b)-i), the outer surface of the object acts as the substrate for the thin polymer film. In some aspects, at least the outer surface of the object comprises a material selected from the group consisting of aluminum oxide, germanium, and silicon. In some aspects, at least the outer surface of the object comprises a material selected from the group consisting of tungsten carbide, silicon, copper, sapphire, and glass. In some aspects, at least the outer surface of the object comprises a material is selected from the group consisting of titanium, titanium cobalt, stainless steel, cobalt-chromium alloys, and titanium/cobalt mixed metal.

The object is not particularly limiting. In some aspects, the object can be an artificial human body part, a cutting tool or a jewelry piece. In some aspects, the object can be a blade or a drill bit. In some aspects, the object can be an artificial hip, knee, ankle, wrist, shoulder, and elbow. In some aspects that object can be sapphire windows and mobile device screens.

In some aspects, applying the thin polymer film to at least a portion of the object includes 3D printing the thin polymer film on the object.

In some aspects, the wavelength of the conditioning laser pulse and/or conversion laser pulse ranges from 193 nm to 308 nm, and the duration of the conditioning laser pulse and/or conversion laser pulse ranges from 20 ns to 60 ns.

In some aspects the object can be a blade or drill bit. In some aspects the object can be an artificial body part such as a hip, knee, ankle, wrist, shoulder, or elbow.

In yet another embodiment of the invention, a process for making a three dimensional object comprises: a) applying a first layer of a thin polymer film on a substrate; b) increasing the absorbance of an unconverted section of the thin polymer film by at least one conditioning laser pulse to produce a lasered section; c) melting the lasered section at a temperature of about 4000K by a conversion laser pulse; quenching the melted lasered section to form an initial quenched section comprising Q-carbon, diamond, and/or graphene; e) adjusting the thin polymer film and at least one quenched section and/or the laser positioning mechanism such that the conditioning laser pulse strikes a subsequent unconverted section of the thin polymer film; f) increasing the absorbance of the subsequent unconverted section of the thin polymer film by the at least one conditioning laser pulse to produce a subsequent lasered section; g) melting the subsequent lasered section at a temperature of about 4000K by the at least one conversion laser pulse; h) quenching the melted subsequent lasered section to form a subsequent quenched section comprising Q-carbon, diamond, and/or graphene; i) repeating steps e) through h) until a final desired portion of the thin polymer film is converted to a finished quenched section, wherein the finished quenched section comprises the initial quenched section and each of the subsequent quenched sections; j) applying a subsequent layer of the thin polymer film in a predetermined pattern to form the object and repeating steps b) through i); and k) repeating step j) until the three-dimensional object is completed. Steps b) through d) and steps f) through h) occur in an environment at ambient temperature and pressure. The polymer film comprises a polymer selected from the group consisting of polyethylene (PE), polyvinyl chloride (PVC), polytetrafluoroethylene (PTFE), polystyrene (PS), and/or polypropylene (PP).

It is to be understood that the various aspects of the thin polymer film; the increasing of the absorbance by at least one conditioning laser pulse; the melting of the lasered section by a conversion laser pulse; the quenching of the melted laser section to form a quenched section comprising Q-carbon, diamond, and/or graphene; the forms of diamonds; the characteristics of the conditioning laser pulse and the conversion laser pulse; the environment at ambient temperature and pressure; and the final desired portion of the polymer film converted, described herein above, apply to the present embodiment as well.

In some aspects, the process further comprises separating the substrate from the three-dimensional object. In some aspects, step a) is completed for the first layer of the thin polymer film before steps b) through i) occur. In some aspects, step j) is completed for the subsequent layer of the thin polymer film before steps b) through i). In some aspects, steps a) and steps b) through i) are performed in tandem. In some aspects, step j) and steps b) through i) are performed in tandem.

In some aspects, the applying of step a) and/or the applying of step j) is done by 3D printing. In some aspects, the finished quenched section is contiguous.

In some aspects, the wavelength of the conditioning laser pulse and/or conversion laser pulse ranges from 193 nm to 308 nm, and the duration of the conditioning laser pulse and/or conversion laser pulse ranges from 20 ns to 60 ns.

In some aspects, the three-dimensional object is an artificial body part, a cutting tool or a jewelry piece.

To highlight the phase transformation of PTFE on nanosecond laser irradiation, a shadow mask is utilized to selectively convert a PTFE block into diamond, while the rest of the region remains masked. PLA processing at 1.0 J/cm$^2$ energy density transforms amorphous PTFE tape into diamond film and nanodiamonds. As this transformation occurs at ambient conditions, the phase transformation is strictly governed by undercooling achieved during ultrafast melt regrowth. FIG. 1(a) highlights the low-resolution SEM micrograph revealing the rapid nucleation of diamonds at the irradiated region while the non-irradiated PTFE film is preserved with a sharp boundary 102. As the diamonds grow extremely fast laterally, with the tendency to undergo island growth, they generally form nano and microrods. On tilt correcting to 50°, the clear laser annealing boundary 104 between the diamond rods and amorphous carbon is revealed in FIG. 1(b). The polymeric PTFE first unzips into monomers and dimers with conditioning laser irradiation pulses, with the absorbance increasing with each subsequent pulse. Finally, the absorbance becomes high enough for the film temperature to reach ~3823 K and form the carbon melt upon the application of the conversion laser irradiation pulse. Compared to equilibrium based thermally driven reduction processes, this carbon melt formed by PLA processing quenches back in less than 100 ns. This leads to minimal interdiffusion and the formation of sharp phase boundaries. Generally, prolonged exposure of polymer coatings to high temperatures results in sublimation and material loss, before it can be graphitized or converted into diamond. As PLA processing entails uniformity in the melt front and the unidirectional heat flow, the regrown diamond films are expected to be homogenous and single-crystalline. FIG. 1(c) reveals the high-resolution SEM micrograph for the nanodiamond rods. The rod-like characteristics of these diamonds suggest anisotropic growth along the <110> chains of diamond. Contrastingly, the morphology of as-acquired PTFE tape remains unchanged, suggesting no presence of diamonds before PLA processing, as shown in 50° tilt-corrected SEM imaging in the backscattering mode in FIG. 1(d).

Figure 2:
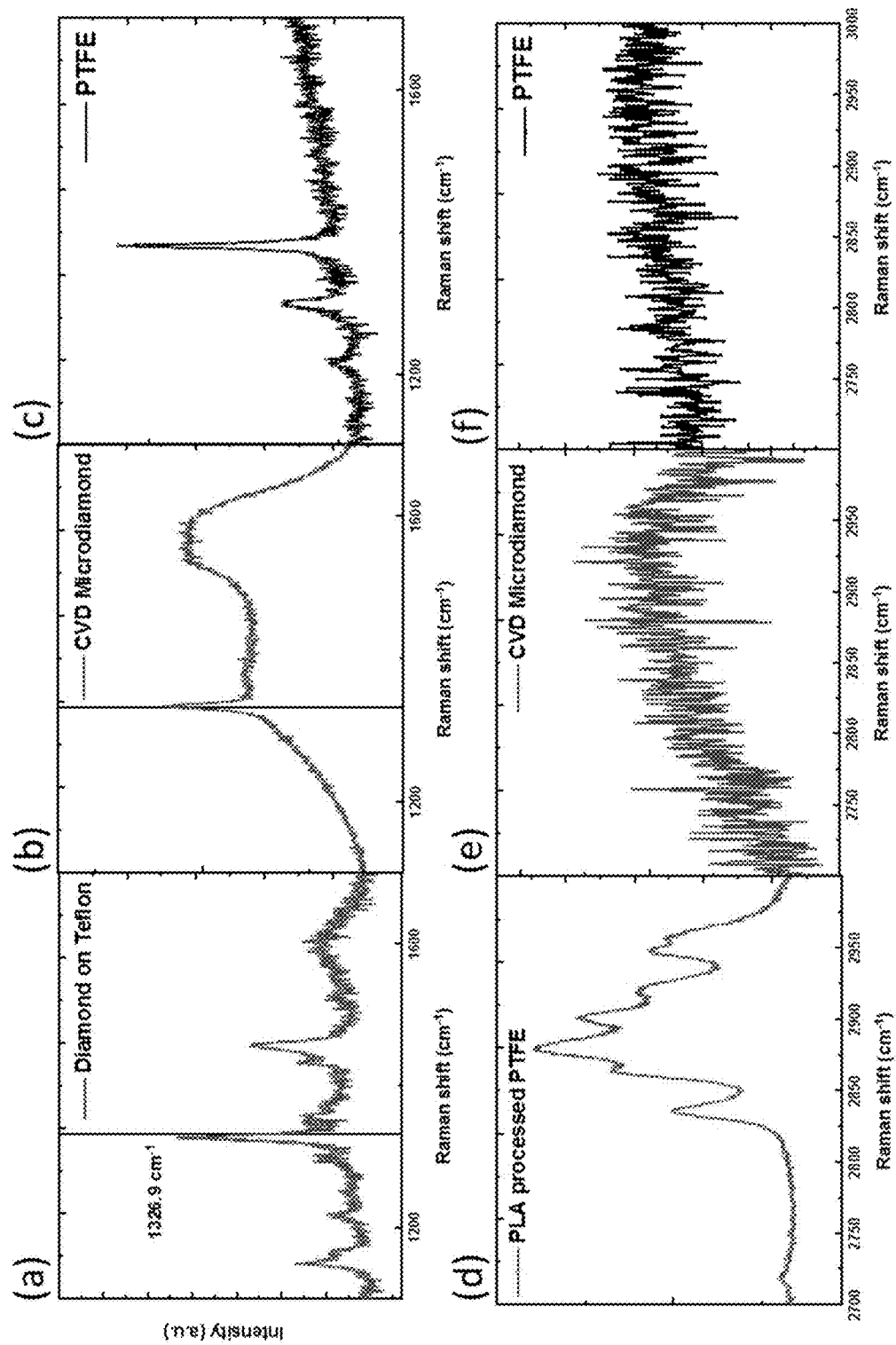
FIG. 2. is a graph depicting an example of Raman spectra results for (a) nanodiamond sheet formed on PLA processing of diamond, (b) HFCVD grown polycrystalline diamond films, (c) as-acquired PTFE tape, while (d) shows the extended Raman modes in PLA processed PTFE tape due to unzipping of polymeric chains, and (e) and (f) reveal that there are no vibrational modes associated with the extended Raman spectra of CVD grown diamond and PTFE tape.

As the polymorphs of carbon exhibit strong Raman modes, the bonding characteristics of diamond films and PTFE are analyzed with Raman spectroscopy in FIG. 2. Amorphous carbon has broad D and G peaks located at 1350 cm$^{-1}$ and 1559 cm$^{-1}$, respectively. In the case of diamond, the interpenetrating FCC lattices result in $T_{2g}$ peak at 1332 cm$^{-1}$. The C—C bond stretching in sp$^2$ hybridized carbon atoms results in the emergence of vibrational G peak. The D-peak (around 1355 cm$^{-1}$) manifests from lattice distortions and spa-like defect formation. The Raman spectrum for PLA processed films in FIG. 2(a) reveals a major peak at 1326.9 cm$^{-1}$, characteristic of the diamond phase. An absence of peaks at 1550 cm$^{-1}$ (graphitic carbon) and 1133 cm$^{-1}$ (nanocrystalline diamond) is indicative of the high quality of the diamond film. Also, no peak is noted at 1480 cm$^{-1}$, eliminating the presence of trans-polyacetylene (TPA). In the case of diamond films, a red-shift is associated with phonon confinement, while a blue-shift arises due to strain considerations. Hence, the shift of 5.1 cm$^{-1}$ is a result of phonon confinement along the z-axis in the diamond sheet. In comparison, the microdiamond films formed by HFCVD processing FIG. 2(b), result in $T_{2g}$ peak at 1332 cm$^{-1}$. The HFCVD processed films exhibit a prominent G peak near 1550 cm$^{-1}$, which is non-existent in the case of PLA processed diamond films. After PLA, there are additional peaks noted at 1170 cm$^{-1}$, 1363 cm$^{-1}$, 1432 cm$^{-1}$ and 1458 cm$^{-1}$. FIG. 2(c) reveals the Raman spectrum for PTFE with vibrational modes at 1215 cm$^{-1}$, 1300 cm$^{-1}$, and 1380 cm$^{-1}$. These vibrational modes arise due to the asymmetric $E_2$ (1215 cm$^{-1}$) and symmetric $E_1$ (1300 cm$^{-1}$) CF$_2$ stretching modes. Notably, the mode at 1380 cm$^{-1}$ arises from depolarized $A_1$ symmetric CF$_2$ mode and has the most marked effect on the decrease in crystallinity. As can be noted from the inset in FIG. 1(c), the tailing, and deviation from the Lorentzian is a result of disorder and amorphization. These residual peaks match well with the Raman spectra of CH$_3$—CH$_2$F, with vibrational modes arising at 1170 cm$^{-1}$ (A'), 1365 cm$^{-1}$ (A'), and 1458 cm$^{-1}$ (A'+A''). As none of the PTFE vibrational modes are present in the Raman spectra of PLA processed region (FIG. 2(a)), and they completely matched with $T_{2g}$ peak from the diamond Raman spectrum and fluorinated Ethanes, it establishes a complete conversion of PTFE into unzipped and melt-regrown phases. In this case, the extended modes are also excited, which are labeled as A'' fundamental with the highest Raman scattering at 2879 cm$^{-1}$ and 2921 cm$^{-1}$ for A' fundamental in case of PLA processed films (FIG. 2(d)) which are not observed in the extended Raman spectrum for HFCVD diamonds (FIG. 2(e)) and PTFE (FIG. 2(f)).

Figure 3:
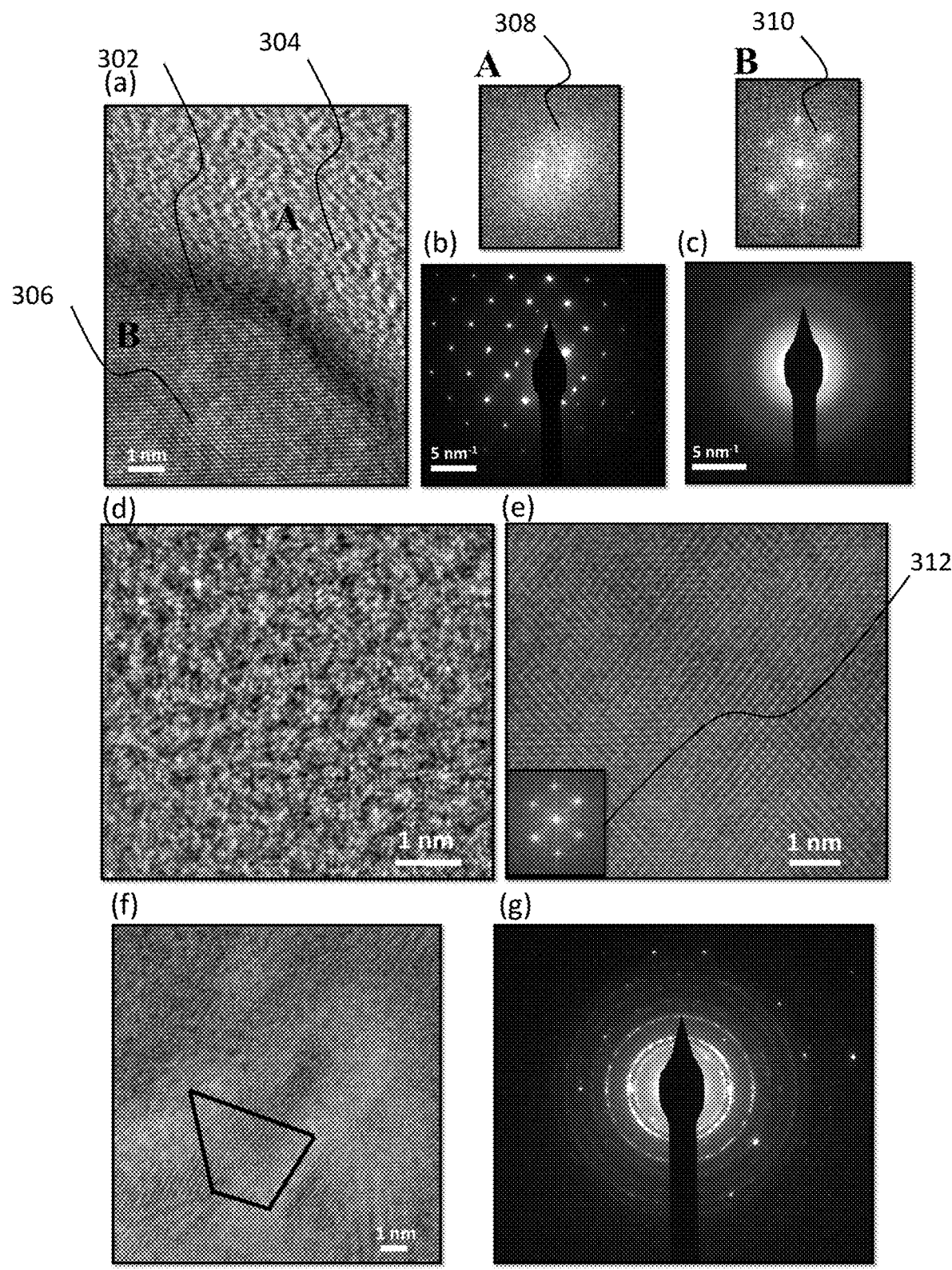
FIG. 3(a) is a plan view of a high-resolution transmission electronic microscope (HHTEM) image revealing the atomically-sharp interface between <110> oriented diamond sheet and amorphous PTFE tape, the inset in A and B reveal the fast Fourier transform (FFT) pattern acquired from amorphous PTFE and PLA processed diamond, (b) and (c) reveal the associated selected area diffraction (SAED) pattern showing the (111) and (200) spots for single-crystalline diamond nanosheet and amorphous nature of PTFE tape with diffused rings, respectively, (d) reveals the HRTEM micrograph for amorphous PTFE with short-range ordering, (e) shows the HRTEM micrograph of single-crystalline diamond with (111) cross lattice fringes and associated FFT pattern in the inset, (f) and (g) reveal the formation of nanodiamonds and corresponding SAED pattern (concentric rings with speckled pattern) acquired from the PLA processed PTFE tape at 0.8 $J/cm^2$.

The conversion of amorphous PTFE tape into diamond is investigated by analyzing the atomic structure with plan-view HRTEM imaging and selected area microdiffraction pattern, as shown in FIG. 3(a). TEM mode in S/TEM microscope is used in this analysis, which has a better information limit than the conventional TEM, with a bigger probe size than in STEM mode to prevent damage of the graphitic planes under the intense 200 keV electron beam. The as-acquired HRTEM image of the film in at <110> zone-axis reveals an atomically-sharp interface 302 between amorphous PTFE 304 and crystalline diamond 306, which provides direct evidence of the first-order phase transformation of amorphous PTFE tape into diamond sheet upon nanosecond PLA processing. The low thermal conductivity of PTFE tape assists in achieving uniform undercooling of the molten carbon to convert it into diamond on regrowth.

The out-of-plane <110> orientation of the diamond sheet is related to rapid unseeded crystallization rather than seeded <111> growth through in-plane epitaxy on <0001> Al$_2$O$_3$. The d-spacing along the (111) planes for diamond is ~2.06 Å which agrees well with the HRTEM imaging analysis. The fast Fourier transform (FFT) patterns for amorphous PTFE 308 and diamond 310 shown in FIG. 3 reveal the distinct diffraction spots (111 and 200) for the crystalline diamond, while PTFE exhibits diffused rings highlighting its amorphous nature. The selected-area diffraction pattern shown in FIG. 3(b) was acquired from the single-crystalline diamond region 306, and presents no evidence for the remanence of the amorphous carbon phase or PTFE. It reveals sharp diffraction spots, with the primary spots indexed as (1-11) and (11-1) family of planes, while (200) spots are kinematically forbidden, arising from double electron diffraction from (1-11) and (11-1) planes. The fact that SAED contains high-order Bragg reflections like (800) is indicative of good crystallinity. As expected, the high-resolution imaging of PTFE tape shown in FIG. 3(d) does not show any consistent lattice fringes due to its amorphous nature, which is also reflected in the associated SAED pattern revealed in FIG. 3(c). On imaging the periphery of PLA boundary, nanodiamond formation is observed, as revealed in the high-resolution HRTEM micrograph in FIG. 3(d). It shows the lattice fringes arising from (111) family of planes from nanodiamond thin film. The FFT pattern matches well with the shown SAED pattern 312 in FIG. 3(e), containing the (111) and (200) spots.

Figure 4:
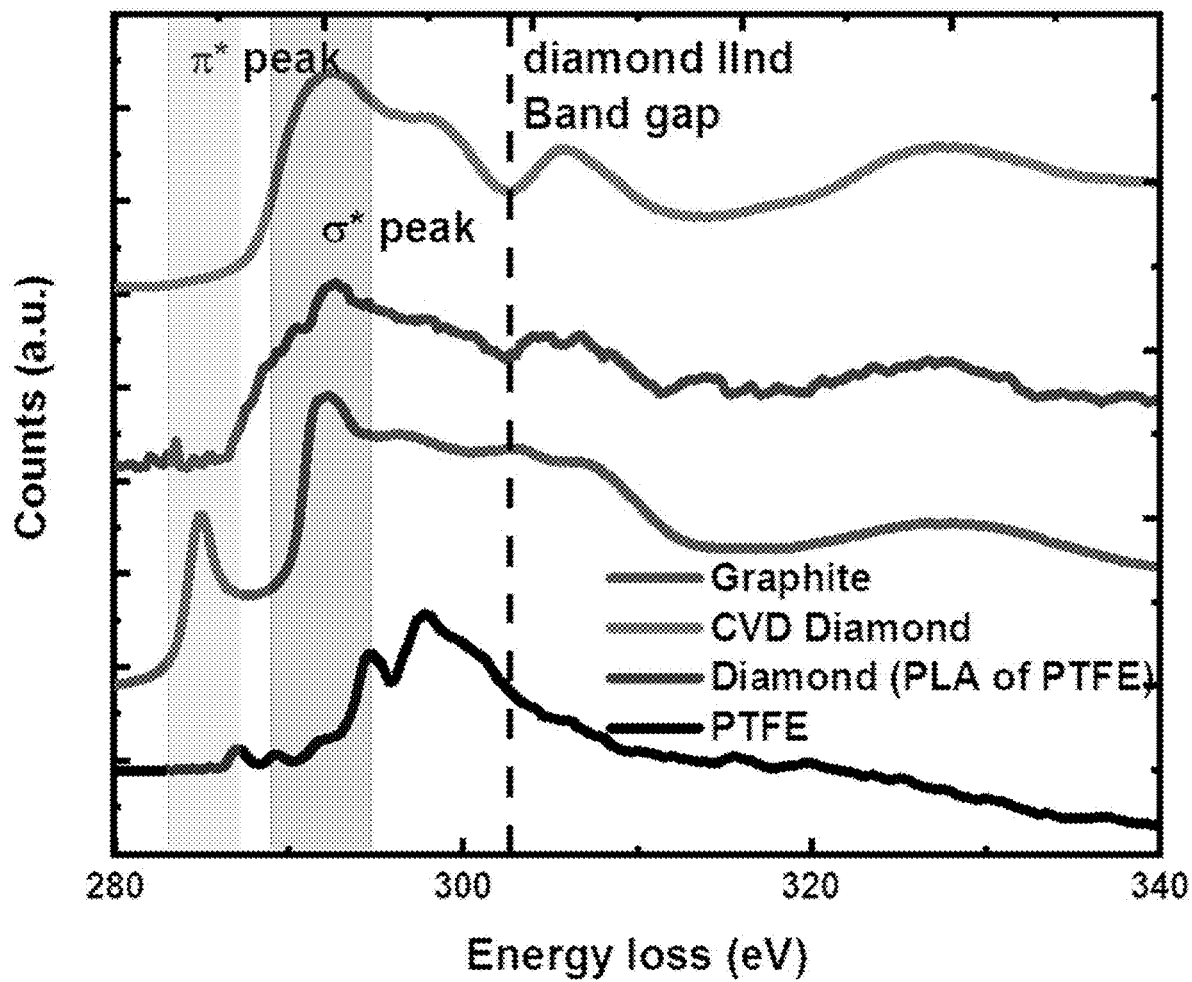
FIG. 4. is a graph revealing the acquired electron energy loss (EEL) spectrum from diamond nanosheet, bulk microdiamonds, amorphous PTFE tape, and graphite.

To further confirm the formation of the diamond from PTFE, high-resolution EELS scans were performed near the diamond/PTFE interface and are shown in FIG. 4. In the EEL spectra of amorphous PTFE, the C-K edge exhibits sharp peaks at ~287, 289 eV arising from the 1 s→π* electronic excitation, while the peak at 292.2 is broadened due to the overlap of conduction bands. The peaks at 294.6, 297 eV arise at much higher intensities due to the 1 s→π* excitation arising from C—C and C—F bonds. The peak near 299.6 eV is related to the near-edge fine structure arising from the nearest neighbor C—C bonded atoms along the polymeric chain. In the case of EEL spectra for carbon polymorphs, the initial peak arises from the π* antibonding electronic states, whereas the second peak corresponds to σ* antibonding states. The electronic transition from 1 s core states to π* and σ* in carbon polymorphs are reflected in the first and second core-loss EEL spectral peaks, respectively. The formation of diamond sheets is further confirmed by studying their electron energy loss spectra (EELS). As shown in FIG. 4, a strong 1 s-2p(π*) transition at ~284 eV is observed in graphene, whereas in the case of nanodiamonds the EEL signature is dominated by the 1 s-2p(σ*) transition at ~297 eV. The absence of π* peak in the diamond phase reflects its phase-pure crystalline nature, also suggesting that amorphous Q-carbon has not formed during PLA processing. The sharp σ* antibonding peak at ~290 eV is a signature for diamond formation, is noted in both CVD grown microdiamonds and PLA processed nanodiamond sheets. The broad humps near 297, 305, and 326 eV are post-edge structures associated with diamond EEL spectrum. There is also a characteristic drop at 302 eV, which corresponds to the absolute second bandgap in diamond. Post-edge states (>290 eV) arise from the electronic density of states (eDOS), which are dependent on the post-edge extended fine structure of diamond.

Together with diamond films, nanodiamonds embedded in disordered graphene are also formed at PLA energy density of 0.8 J/cm$^2$. The presence of disordered sp$^2$ bonded carbon with nanodiamonds suggests close-to surface melting. The HRTEM image for nanodiamond with cross lattice fringes is shown in FIG. 3(f). For nanodiamonds, the SAED pattern shows a characteristic speckled, concentric ring pattern with the distinct diffraction peaks arising from (111), (200), (220), (311), (222), (004), (331), and (333) planes, as shown in FIG. 3(g). Interestingly, during PLA processing when diamond nucleates under the highly undercooled conditions from Q-carbon, the microcrystallites are heavily twinned. The characteristic twinned diamonds exhibit multiple diffraction spots with the presence of twin planes along the (111) twin boundary and a <110> twin axis. Here, the out-of-plane orientation is <110>, but crystallographic twins are not observed in both microcrystallites and nanocrystallites of PLA regrown diamonds. Similar results have been observed on PLA experiments performed on other DCL systems like silicon and germanium, resulting in liquid-phase regrowth of several nanometer wide nanocrystalline from the superundercooled state of Si. These silicon nanocrystallites provide nucleation sites for further growth of silicon microcrystallites. Comparing these results with the observations in silicon, it is apparent that the undercooling achieved in this case is significantly lower than the critical undercooling required for amorphization, and regrowth velocity is expected to be 4-6 m/s. Notably, previous experiments on PLA processing of $_{73}$Ge$^+$ and $_{75}$As$^+$ implanted highly oriented pyrolytic graphite (HOPG) crystals using a ruby laser (energy density=0.6-3.0 J cm$^{-2}$, wavelength=693 nm, pulse duration=30 ns) did not result in diamond conversion. This is due to the presence of highly (thermally) conducting HOPG layers, which produced little or no undercooling. In this case, the amorphous PTFE melts and retains its structure at 200-300 K less than the melting point of crystalline graphite during ultrafast melt quenching, to create the undercooled liquid carbon. Upon subsequent quenching of this undercooled state, diamonds are nucleated. At these transition temperatures (~4000 K), Gibbs free energy of undercooled molten carbon equals that of the diamond. This undercooling forces the molten carbon to exist at temperatures near melting point of diamond, stabilizing its nucleation. Therefore, this undercooled state is important for the nucleation of nanodiamonds, even in polymeric materials like PTFE.

Figure 5:
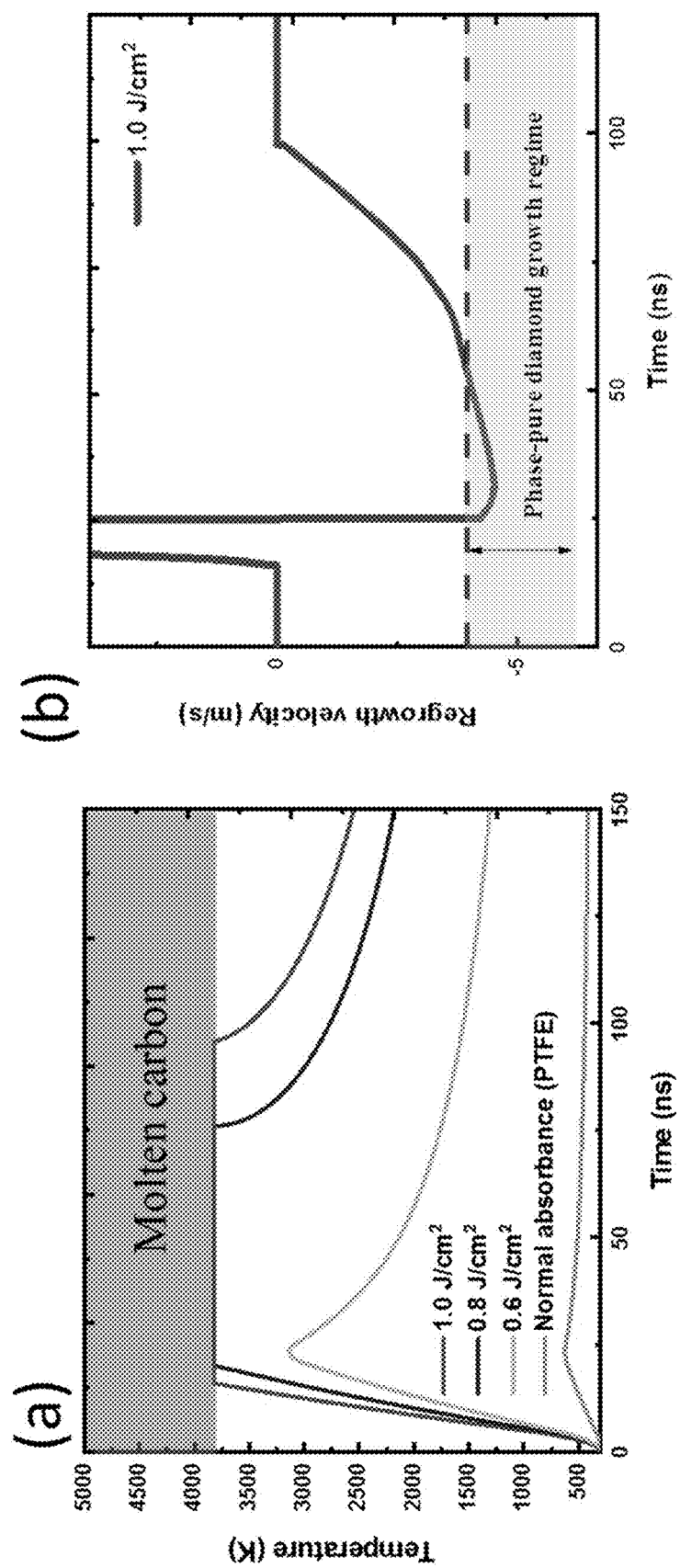
FIG. 5(a) is a graph showing the temperature-time SLIM plots for as-acquired PTFE tape at various PLA energy densities and with absorbance changeover on structural degradation and unzipping, and (b) is a graph showing the carbon melt depth vs. time for PLA energy density of 1.0 $J/cm^2$.

The melting kinetics during PLA was studied using a simultaneous temporal and spatial Gaussian as the heat source. The laser-solid interactions were analyzed by SLIM programming to understand the phase transformation of amorphous PTFE into diamond. The specimen boundary conditions were approximated as adiabatic, with thermal losses (radiative and conductive) integrated into PLA simulations. Once surface melting occurs, the melt-front propagates towards the substrate, with the conduction losses driving it forward. The solid-phase regrowth was simulated by analyzing phase transformation across the solid/liquid interface. As the irradiation spot size is laterally much larger than the melt depth, column approximation is employed to simplify the laser-solid interactions. This approximation is feasible as the normal heat flux is an order of magnitude higher than the in-plane thermal flux. The laser parameters—$\lambda$=193 nm, FWHM=20 ns, corresponding reflectivity for as-deposited amorphous carbon, and molten carbon were used as input parameters to simulate PLA. The laser parameters and thermal conductivities of the substrate and thin film are shown to be the important parameters for achieving the required super undercooling. The parameters used for the SLIM simulation for Teflon/c-Al$_2$O$_3$ system were: 3823 K as melting point, 7000 K as evaporation point, 19775 J/cm$^3$, the absorption coefficient for molten carbon is 8×10$^5$ and laser pulse-width of 20 ns. Once melting occurs, the physical properties of molten carbon are utilized, as above 3000 K, PTFE completely disintegrates into carbon with F$_2$ evolution. The thermal conductivity of molten carbon is 290 W/mK, and that of amorphous PTFE is 0.25 W/mK. The reflectivity in the solid and liquid state is 0.05 and 0.7, respectively. Interestingly, the low absorption coefficient of pristine crystalline PTFE in the UV regime (250 cm$^{-1}$ at 193 nm) results in non-melting even in the case of PLA energy density as high as 1 J/cm$^2$ as shown in FIG. 5(a). This low absorption is a result of the high optical band gap of PTFE tape (6.00 eV+ electron affinity of 2.2 eV), while the irradiation laser energy is 6.42 eV. In our case, we were able to irradiate and melt PTFE successfully due to the usage of white amorphous PTFE tape as the associated mid-gap states help in increasing absorption with the occurrence of the two-photon process.

Successful ablation of PTFE (due to evaporation) and occurrence of residual graphitic carbon has been noted on irradiation with nanosecond lasers under wavelengths as high as 248 nm. Notably, photon energy absorption and polymer degradation have been shown to compensate for the reduced absorption coefficient. The first laser pulse, even at 1.6 J/cm$^2$, did not lead to any ablation or surface reconstruction. However, the second pulse and after that resulted in an absorption coefficient of 15000 cm$^{-1}$. Here, the effective absorption coefficient is given as: $a_{eff}=a_0+Na_j$ with $a_0$ as the absorption coefficient for un-irradiated PTFE tape and $a_j$ is the absorption coefficient induced by a single pulse. For single-photon processes, $a_j$ is proportional to laser fluence. As in our procedure, we operated at 0.8-1.0 J/cm$^2$ laser fluence, an absorption coefficient of 7500 cm$^{-1}$ was utilized. Notably, the findings resulted in an ablation threshold of 4.0 eV per monomer, hence on degradation and unzipping of the CF$_2$ chains, the absorption coefficient increases as the process becomes single-photon-absorption driven.

The temperature-time profiles shown in FIG. 5(a) suggest 0.8 J cm$^{-2}$ as the threshold energy density (E$_d$) to melt amorphous PTFE tape on Al$_2$O$_3$. To achieve phase transformation amorphous PTFE into crystalline diamond or superhard Q-carbon, it is required to first achieve the melting of carbon. As PLA is an ultrafast process, it is ideal for analyzing melting in carbon which sublimates during equilibrium-based processing under elevated temperatures. The molten carbon is metallic in nature, with thermal conductivity of 2.9 Wcm$^{-1}$K$^{-1}$. The extent of undercooling in molten carbon controls the regrowth of graphene, diamond, or Q-carbon. The low undercooling affects the regrowth of thermodynamically stable graphite. At E$_d$=0.8 J/cm$^2$, the surface melting of amorphous PTFE occurs. This condition is ideal for regrowth of nanodiamonds with graphene-related materials. FIG. 5(a) reveals that carbon melting occurs as the film reaches 3823 K temperatures. On termination of the laser pulse, as no increment heat flux, the melt front recedes. Post onset of melting, FIG. 5(b) reflects a rise in melt depth with an increase in melt lifetime, at PLA energy density of 1.0 J/cm$^2$. Notably, the formation of high-quality diamond sheets is underpinned by the uniform undercooling associated with the carbon melt, which subsequently undergoes ultrafast quenching, which does not provide the film any opportunity to form wrinkles and point defects. Theoretical and experimental results suggest that the local bonding in molten carbon varies from two-to-threefold coordination at mass density ~1.27 g/cm$^3$, while it changes to fourfold coordination atoms under the higher density of 3.02 g/cm$^3$.

The ab-initio MD simulations are performed by melting carbon and then quenching the melt under isotropic pressure. Once the temperature reaches 2000 K, the pressure is released to 760 Torr. Before quenching the melt, it was equilibrated using a Nose-Hoover thermostat. The liquid carbon was cooled rapidly under the canonical (NVT) ensemble conditions, using a Langevin thermostat. The quenched structure was relaxed by utilizing 10$^{-4}$ Ry/Bohr force convergence criterion. This liquid quench method is classically utilized to model metastable structures on liquid-phase ultrafast quenching.

Figure 6A:
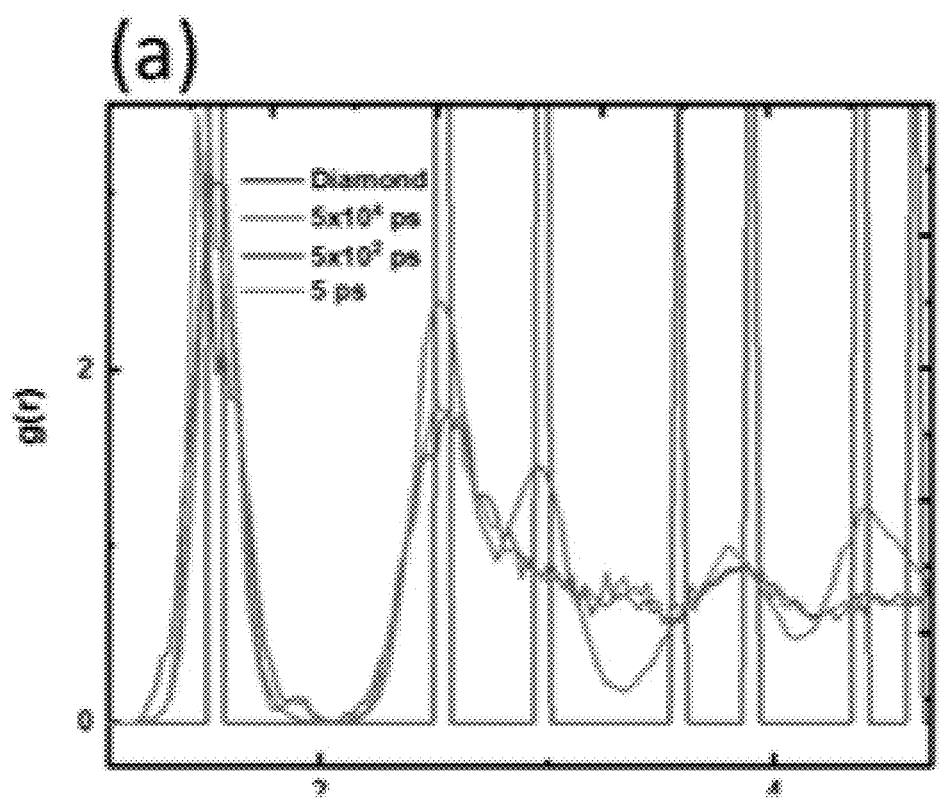
FIG. 6(a) is a graph highlighting the modifications in short-range ordering during melt regrowth for carbon melt with radial distribution function plots under 50 GPa pressure, as a function of quenching rates.

As the undercooling considerations are hard to manifest in MD simulations, external isotropic pressure was used to densify the molten carbon. In the case of ultrafast processing, the undercooling of the melt is critical in controlling the final quenched structure. The modifications in the structure of molten carbon on quenching are analyzed using the radial distribution function (rDF) profiles, shown in FIG. 6(a), under isotropic pressure of 50 GPa by modulating the quench rates to study the tetrahedral structural evolution as a function of melt lifetime. FIG. 6(a) reveals the increase in ordering as the melt lifetime increases from 25 ps, 250 ps, and 50 ns. The coordination number (CN) reflects the dominant hybridization state of the quenched structure.

Figure 6B:
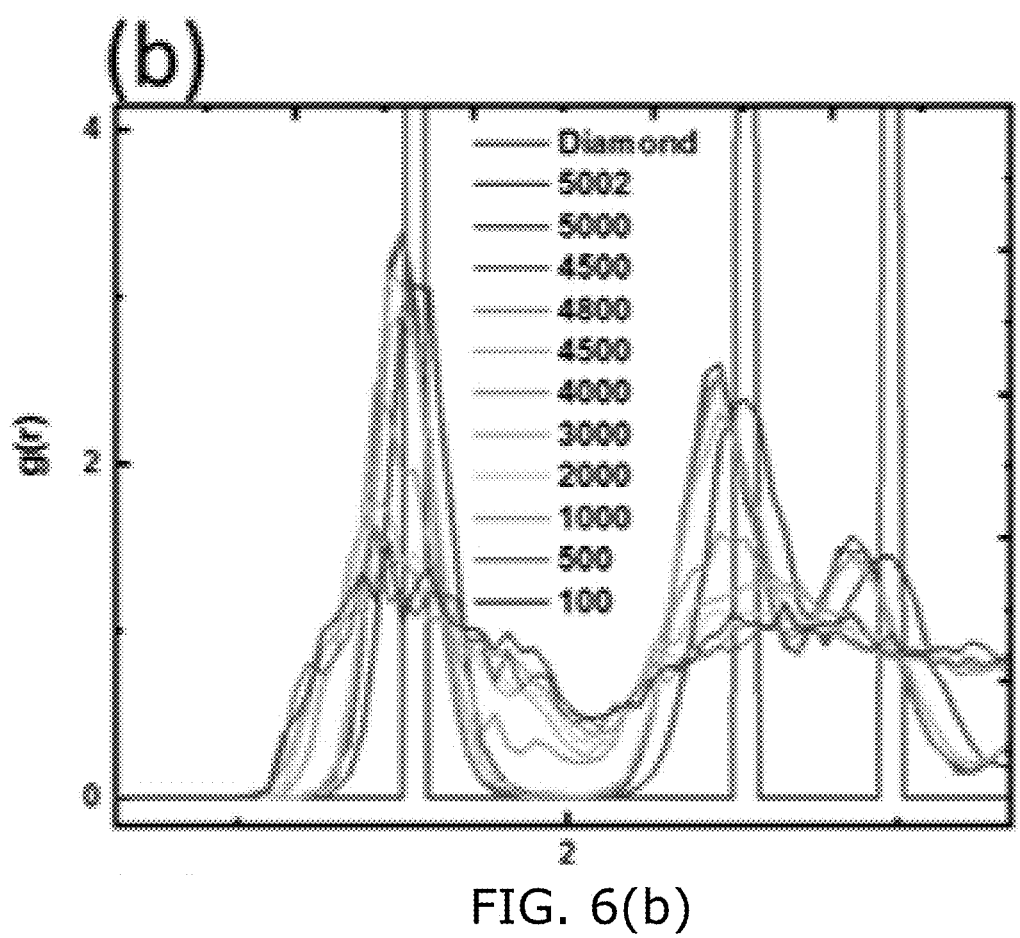
FIG. 6(b) is a graph highlighting the changes in radial distribution function as carbon undergoes melting and subsequent quenching, forming tetrahedral carbon.
Figure 6C:
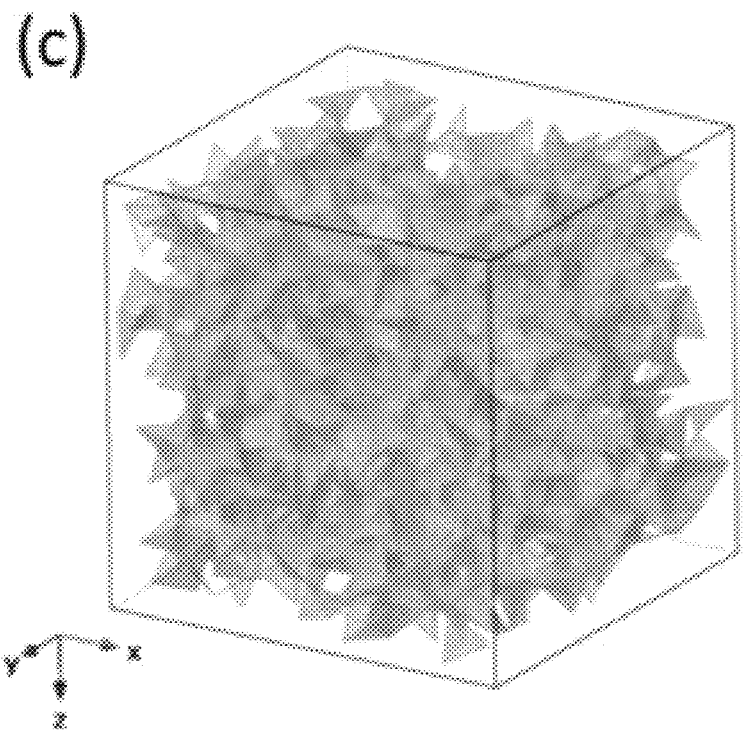
FIG. 6(c) is a schematic showing the simulated structure of melt regrown tetrahedral carbon.
Figure 6D:
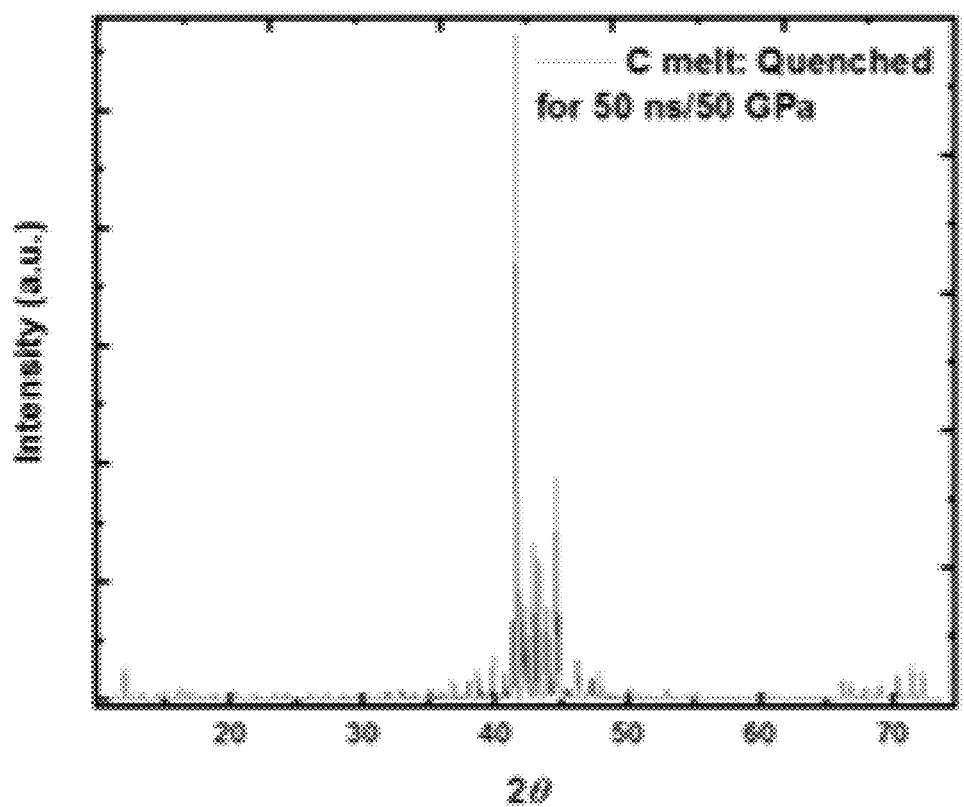
FIG. 6(d) is a graph showing the calculated x-ray diffraction (XRD) pattern of densified tetrahedral carbon upon melt quenching showing broad peak near 2θ of 41.5°.

Using the radial cutoff as 1.85 Å in rDF profiles, molten carbon quenched under 50 GPa, results in a disordered amorphous structure with ~98% $sp^3$ content, suggesting the formation of the recently reported amorphous diamond. These pressure-dependent quenched structures are consistent with the super-undercooling driven phase transformation of molten carbon into densely-packed Q-carbon and diamonds. FIG. 6b shows the evolution in rDF of carbon melt as a function of simulation timesteps. At the onset of melting, a hump is noted, suggesting the evolution of disordered liquid carbon. As the timesteps increase (30-60), the system entropy decreases during the pressurized quench, resulting in a reduction in disorder and conversion into tetrahedrally bonded carbon. FIG. 6(c) shows the simulated structure of the ordered tetrahedrally bonded structure formed on quenching for 50 ns ($10^{11}$ K/s quench rate), with its powder diffraction pattern revealing the major peak at 2θ=41.5° (2θ for (111) reflections for bulk diamond is =43.9°, as shown in FIG. 6(d). These simulations show that amorphous carbon can be converted into nano and microdiamonds on ultrafast melt quenching, depending on the ambient conditions and melt quench lifetime.

Figure 7:
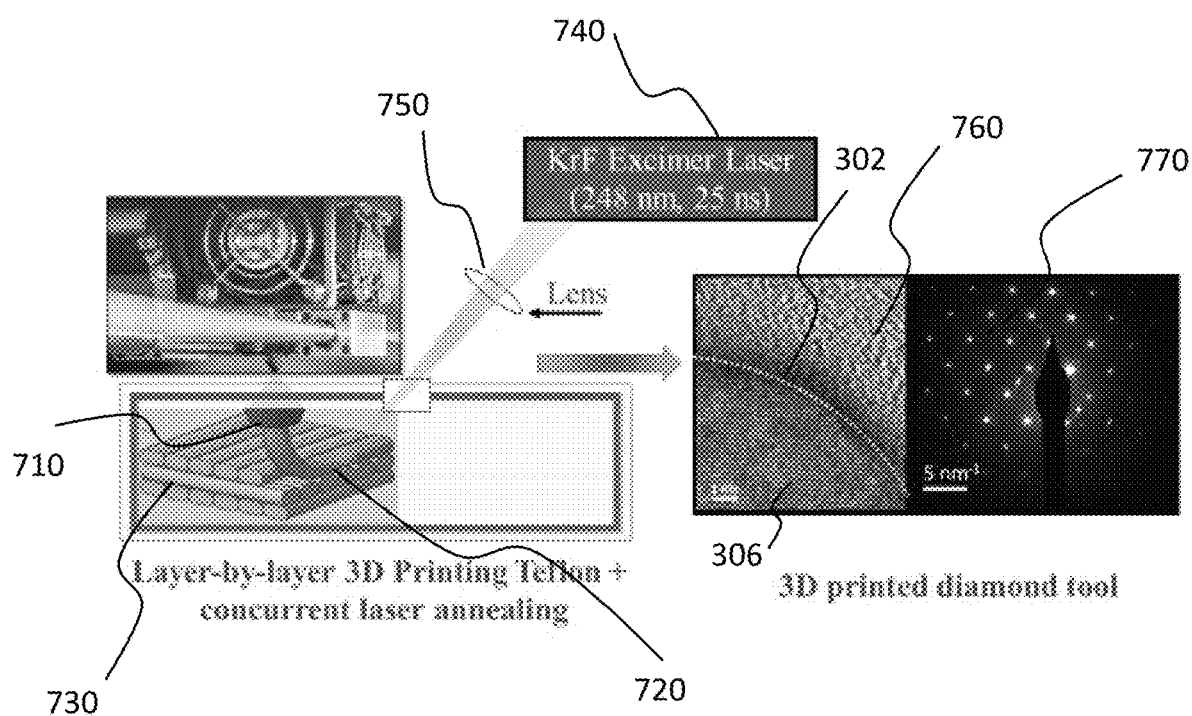
FIG. 7 is a schematic showing the layer-by-layer 3D printing of Teflon and the concurrent laser annealing and the corresponding HRTEM micrograph and SAED pattern.

FIG. 7 shows a snapshot illustrating a non-limiting embodiment of producing a three-dimensional object using the inventive process. A 3D printer is used to build the three-dimensional object. Printer nozzle 710 is adding a thin polymer film layer 720 to the three-dimensional object 730. In tandem to the 3D printing, KrF excimer laser 740, irradiates 248 nm wavelength for 25 ns. The laser pulses pass through lens 750 and strike a section of the new layer of polymer film 720. With the laser pulses and quenching, the now converted section of the new layer of polymer film 720 comprises diamond, Q-carbon, and/or graphene. The SEM micrograph 760 is a repeat of FIG. 3a and shows the border 302 between the quenched section comprising crystalline diamond and the converted PTFE thin film. The selected-area diffraction pattern 770 is a repeat of FIG. 3b and was acquired from the single-crystalline diamond section 306 and presents no evidence for the remanence of the amorphous carbon phase or PTFE.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A process comprising:
   a) increasing absorbance of an unconverted section of a polymer film by at least one conditioning laser pulse to produce a lasered section;
   b) melting the lasered section at a temperature of about 4000K by a conversion laser pulse; and
   c) quenching the melted lasered section to form an initial quenched section comprising Q-carbon, diamond, and/or graphene,
   wherein steps a) through c) occur in an environment at ambient temperature and pressure, and
   wherein the polymer film comprises a polymer selected from the group consisting of polyethylene (PE), polyvinyl chloride (PVC), polytetrafluoroethylene (PTFE), polystyrene (PS), and/or polypropylene (PP).

2. The process of claim 1, wherein the polymer consists of PTFE.

3. The process of claim 1, wherein the wavelength of the conditioning laser pulse and/or the conversion laser pulse ranges from 193 nm to 308 nm, and wherein the duration of the conditioning laser pulse and/or the conversion laser pulse ranges from 20 ns to 60 ns.

4. The process of claim 1, wherein the initial quenched section comprises a composite of Q-carbon and diamond.

5. The process of claim 1, wherein the polymer film is a part of a polytetrafluoroethylene tape.

6. The process of claim 1, wherein the polymer film is proximate to a substrate, wherein the substrate is selected from the group consisting of metals, semiconductors, ceramics, and glass.

7. The process of claim 6, wherein the polymer film and the substrate are in a form of a tape.

8. The process of claim 6, wherein the substrate is an object, and the polymer film is a coating encompassing the object.

9. The process of claim 1, further comprising:
   d) adjusting the polymer film and the at least one quenched section and/or the laser positioning mechanism such that the conditioning laser pulse strikes a subsequent unconverted section of the polymer film;
   e) increasing the absorbance of the subsequent unconverted section of the polymer film by the at least one conditioning laser pulse to produce a subsequent lasered section;
   f) melting the subsequent lasered section at a temperature of about 4000K by the conversion laser pulse;
   g) quenching the melted subsequent lasered section to form a subsequent quenched section comprising Q-carbon, diamond, and/or graphene; and
   h) repeating steps d) through g) until a final desired portion of the polymer film is converted to a finished quenched section, wherein the finished quench section comprises the initial quenched section and each of the subsequent quenched sections;
   wherein steps e) through g) occur in an environment at ambient temperature and pressure.

10. The process of claim 9, wherein the finished quenched section is contiguous, and wherein the final desired portion of the polymer film converted to the finished quenched section ranges from 10% to 100%.

11. A process for coating an object comprising:
    a) applying a polymer film to at least a portion of the object;
    b) increasing the absorbance of an unconverted section of the polymer film by at least one conditioning laser pulse to produce a lasered section;
    c) melting the lasered section at a temperature of about 4000K by a conversion laser pulse;
    d) quenching the melted lasered section to form an initial quenched section comprising Q-carbon, diamond, and/or graphene;
    e) adjusting the object with the applied polymer film and the at least one quenched section and/or the laser positioning mechanism such that the conditioning laser pulse strikes a subsequent unconverted section of the polymer film;
    f) increasing the absorbance of the subsequent unconverted section of the polymer film by the at least one conditioning laser pulse to produce a subsequent lasered section;
    g) melting the subsequent lasered section at a temperature of about 4000K by the conversion laser pulse;
    h) quenching the melted subsequent lasered section to create a subsequent quenched section comprising Q-carbon, diamond, and/or graphene; and
    i) repeating steps e) through h) until a final desired portion of the polymer film is converted to the finished quenched section, wherein the finished quenched section comprises the initial quenched section and each of the subsequent quenched sections, wherein steps b) through d) and steps f) through h) occur in an environment at ambient temperature and pressure, and wherein the polymer film comprises a polymer selected from the group consisting of polyethylene (PE), polyvinyl chloride (PVC), polytetrafluoroethylene (PTFE), polystyrene (PS), and/or polypropylene (PP).

12. The process of claim 11, wherein the applying step a) includes 3D printing the polymer film on the object.

13. The process of claim 11, wherein the wavelength of the conditioning laser pulse and/or the conversion laser pulse ranges from 193 nm to 308 nm, and wherein the duration of the conditioning laser pulse and/or the conversion laser pulse ranges from 20 ns to 60 ns.

14. The process of claim 11, wherein the object is selected from the group consisting of blades and drill bits.

15. The process of claim 11, wherein the object is selected from the group consisting of an artificial hip, knee, ankle, wrist, shoulder, and elbow.

16. A process for making a three-dimensional object comprising:
   a) applying a first layer of a polymer film on a substrate;
   b) increasing the absorbance of an unconverted section of the polymer film by at least one conditioning laser pulse to produce a lasered section;
   c) melting the lasered section at a temperature of about 4000K by a conversion laser pulse;
   d) quenching the melted lasered section to form an initial quenched section comprising Q-carbon, diamond, and/or graphene;
   e) adjusting the polymer film and the at least one quenched section and/or the laser positioning mechanism such that the conditioning laser pulse strikes a subsequent unconverted section of the polymer film;
   f) increasing the absorbance of the subsequent unconverted section of the polymer film by the at least one conditioning laser pulse to produce a subsequent lasered section;
   g) melting the subsequent lasered section at a temperature of about 4000K by the at least one conversion laser pulse;
   h) quenching the melted subsequent lasered section to form a subsequent quenched section comprising Q-carbon, diamond, and/or graphene;
   i) repeating steps e) through h) until a final desired portion of the polymer film is converted to a finished quenched section, wherein the finished quenched section comprises the initial quenched section and each of the subsequent quenched sections;
   j) applying a subsequent layer of the polymer film in a predetermined pattern to form the three-dimensional object and repeating steps b) through i); and
   k) repeating step j) until the three-dimensional object is completed, wherein steps b) through d) and steps f) through h) occur in an environment at ambient temperature and pressure, and wherein the polymer film comprises a polymer selected from the group consisting of polyethylene (PE), polyvinyl chloride (PVC), polytetrafluoroethylene (PTFE), polystyrene (PS), and/or polypropylene (PP).

17. The process of claim 16, wherein the applying of step a) and/or the applying of step j) includes 3D printing the polymer film.

18. The process of claim 16, wherein the wavelength of the conditioning laser pulse and/or the conversion laser pulse ranges from 193 nm to 308 nm, and wherein the duration of the conditioning laser pulse and/or the conversion laser pulse ranges from 20 ns to 60 ns.

19. The process of claim 16, wherein at least one of the finished quenched sections is contiguous.

20. The process of claim 16, wherein the three-dimensional object is selected from the group consisting of an artificial human body part, a cutting tool and a jewelry piece.

* * * * *